United States Patent [19]
McDonald

[11] Patent Number: 6,106,123
[45] Date of Patent: Aug. 22, 2000

[54] VISION AID FOR RECOVERING OPHTHALMIC PATIENTS

[76] Inventor: Patrick L. McDonald, 15 Oaknoll Rd., Wilmington, Del. 19808-3113

[21] Appl. No.: 09/412,749

[22] Filed: Oct. 5, 1999

[51] Int. Cl.⁷ .................................................. G02B 7/182
[52] U.S. Cl. .............................................................. 359/872
[58] Field of Search .................................. 351/245, 246; 359/850, 862, 865, 872, 871, 882

[56] References Cited

U.S. PATENT DOCUMENTS

| | | |
|---|---|---|
| D. 391,278 | 2/1998 | Kung . |
| 1,302,254 | 4/1919 | Warnecke . |
| 1,828,924 | 10/1931 | Chardell et al. . |
| 2,909,959 | 10/1959 | Girden . |
| 5,061,055 | 10/1991 | Dube . |
| 5,148,327 | 9/1992 | Gaxiola, Jr. . |
| 5,408,713 | 4/1995 | Stratton et al. . |
| 5,422,759 | 6/1995 | Lee . |
| 5,471,264 | 11/1995 | Hsia et al. . |
| 5,661,860 | 9/1997 | Heitz . |
| 5,760,865 | 6/1998 | Webster . |
| 5,835,294 | 11/1998 | Minegishi . |
| 5,900,997 | 5/1999 | Shapiro . |
| 6,010,225 | 1/2000 | Lerner et al. ............................ 359/872 |

FOREIGN PATENT DOCUMENTS

| | | |
|---|---|---|
| 2620406 | 3/1989 | France . |
| 820353 | 9/1959 | United Kingdom . |
| 2045453 | 10/1980 | United Kingdom . |

*Primary Examiner*—George Manuel
*Attorney, Agent, or Firm*—Richard C. Litman

[57] ABSTRACT

A vision aid for recovering ophthalmic patients permits the user to maintain the head in a face down position for proper healing of the eye after certain types of ophthalmic surgery, while enabling the user to enjoy a forward view through the device for making eye contact during conversation, watching television, etc. The device comprises a folding box-like structure having a base or floor panel, back wall, and upper panel or lid hinged to the upper edge of the back wall. An object mirror is secured to the inner or lower surface of the lid, with a viewing mirror being secured to the upper or inner surface of the floor panel. When the lid is raised or opened to the proper position, the view from in front of the device reflects from the object mirror in the lid or top, generally downwardly to the viewing mirror in the floor of the box, where the view may be seen by the user looking through a viewport at the back of the lid. Side walls are provided to block lateral ambient light from the mirrors, with the side walls and other structure also serving to lock the lid at the desired open angle. The bottom of the device may be padded for the user to hold the device comfortably upon the lap, and may include a tripod mount for the device to be removably secured to a conventional camera tripod or the like, as desired.

18 Claims, 4 Drawing Sheets

VISION AID FOR RECOVERING OPHTHALMIC PATIENTS

BACKGROUND OF THE INVENTION

1. Field of the Invention

The present invention relates generally to the field of devices and equipment used in medicine and surgery, and more specifically to an optical device providing a generally forward and horizontal field of view for a person looking downwardly into the device. The present invention is particularly useful and valuable for persons who are recovering from ophthalmic surgery, in which an air bubble or the like is introduced into the back of the eye and the recovering patient must keep his/her face and eyes oriented downwardly for proper recovery.

2. Description of the Related Art

Ophthalmic medicine and surgical procedures have made great strides in the recent past, with more and more visual infirmities being curable. Where certain visual problems were very difficult, or impossible, to cure in the past, modern treatments have opened the door to relatively rapid and simple treatment for various problems associated with the eye. As an example, a relatively recently developed treatment for retinal problems (e. g., detached retina and macular degeneration) has been to insert a bubble of air or the like into the eye, where the pressure of the air bubble exerts a restorative force against the retina.

While the above described treatment has proven effective, it is to say the least, inconvenient for the recovering patient. It is essential that the eye be oriented downwardly on the order of eighteen, or perhaps more, hours per day for at least a few weeks, in order to maintain the position of the bubble against the back of the retina during the healing process. The recovering patient i.s required to sleep in a face downward position, and cannot look up to enjoy a normal horizontal field of view for more than a few moments at a time. This precludes the patient from engaging in most normal activities which would be enjoyed by most persons recovering from an injury or illness, including watching television, face to face contact with other persons, etc. A person having such a limitation imposed upon their normal life, is greatly limited in the activities which he/she may enjoy.

Accordingly, a need will be seen for a device enabling a person recovering from such ophthalmic surgery, to enjoy a generally forward and horizontal field of view while maintaining a generally face down orientation. The present vision aid generally comprises a folding box with a generally horizontal inlet and a viewing opening in the top of the box generally opposite the inlet. Two generally opposed mirrors are installed within the box, with the two mirrors providing double reversal of an image entering the box so the image appears upright to the user of the device. The device may be rested upon the lap of the user (the bottom surface may be padded), or may be installed upon a tripod for support, as desired.

A discussion of the related art of which the present inventor is aware, and its differences and distinctions from the present invention, is provided below.

U.S. Pat. No. 1,302,254 issued on Apr. 29, 1919 to Harry W. Warnecke, titled "Observation Device," describes a periscope for a person to look over a relatively low obstruction and observe the field of view beyond. As such, the two mirrors are parallel to one another, and the observer's view is parallel to that gathered by the uppermost mirror. While Warnecke provides for the telescoping of his periscope, the two parallel mirrors and lack of angular change of the field of view, render the Warnecke device unsuitable for use by a person who is required to face downwardly most of the time. Moreover, Warnecke does not provide any means for supporting his periscope other than by hand, whereas the present vision aid is adapted for support on the user's lap or on a tripod, as desired.

U.S. Pat. No. 1,828,924 issued on Oct. 27, 1931 to James J. Chardell et al., titled "Combined Spotlight And Observation Device," describes a periscope including a rear view mirror at one end thereof, and an internal spotlight for projecting light from the device. The Chardell et al. periscope may be telescoped, as in the Warnecke periscope described above, but no means is provided for turning the field of view essentially ninety degrees to provide a generally horizontal field of view for a downwardly looking person, as provided by the present invention. Moreover, the Chardell et al. periscope mounts by means of a permanent bracket, unlike the lap and tripod support of the present vision aid.

U.S. Pat. No. 2,909,959 issued on Oct. 27, 1959 to Barney B. Girden, titled "Swimming Face Mask With Periscope," describes a device having at least one embodiment in which a downwardly looking swimmer may have a generally horizontal field of view through a periscope, with the view being provided at the top of the face mask. The device is worn hands free on the face, and encloses the nose and mouth as well as covering the eyes. Thus, conversation would be impossible with the Girden face mask and periscope, whereas the present device may be supported on the lap or by means of a tripod, allowing the user to converse with others in the area and/or interact in other ways as well. Moreover, no folding or collapsing action is provided for the Girden face mask and periscope, whereas the present viewing device is foldable.

U.S. Pat. No. 5,061,055 issued on Oct. 29, 1991 to Lyne Dube, titled "Bedside Television Viewer," describes a device configured for removable attachment to an overhead lampshade or the like, for a viewer to look upwardly into the device. The Dube device includes a pair of generally facing mirrors which turn the image on the order of ninety degrees, depending upon the adjustment of one of the mirrors. While the Dube device might be generally inverted to allow a person to look downwardly into the device, it cannot be supported on the lap of the user, as such support would block the entrance of the view to the device. Moreover, as the Dube device is supported over the head and body of a person, a tripod support is not feasible for the Dube device, whereas the present vision aid is freely supportable by a tripod if so desired.

U.S. Pat. No. 5,148,327 issued on Sep. 15, 1992 to Miguel Gaxiola, Jr., titled "Forward View Mirror System For Bicycles," describes a mirror system for attachment to the handlebars of a bicycle to enable a forwardly crouching rider to observe the view ahead without tilting the head rearwardly and inducing neck strain. The two mirrors and their attachment structure are essentially permanently mounted to the handlebars or other structure of the bicycle, and cannot be readily removed and transported with the user as desired. Gaxiola, Jr. does not provide any means of enclosing, folding, or supporting his mirror system by lap or tripod, as provided by the present vision aid invention.

U.S. Pat. No. 5,408,713 issued on Apr. 25, 1995 to Paul Stratton et al., titled "Head-Rest," describes various embodiments of a stand for placement on the floor and having a headrest thereatop. A pair of mirrors is installed between the base and the headrest, enabling the user to see forwardly while facing downwardly. However, the Stratton et al. stand cannot be placed upon the user's lap and requires a specialized support frame, whereas the present device may be supported from the floor by means of a conventional camera tripod or the like, thus reducing the cost of the present device in comparison to the Stratton et al. device. Also, while the Stratton et al. device may be disassembled, it is not foldable, as is the present device. Moreover, the present device essentially comprises a box with sides for reducing ambient light or glare, while the Stratton et al. device is completely open.

U.S. Pat. No. 5,422,759 issued on Jun. 6, 1995 to John Lee, titled "Downward Viewing Optical Device," describes a mirror system for wearing about the head (i. e., attachable to an eyeglass frame or headband). The optics of the Lee apparatus are exactly opposite those of the present invention, as a user of the Lee apparatus who carries the head in a forwardly and downwardly lowered position, would be able to see only the area of his/her chest, rather than a view forward, as provided by the present invention. Moreover, Lee does not provide any means for placing his device on a lap or supporting it by means of a tripod, as provided by the present invention.

U.S. Pat. No. 5,471,264 issued on Nov. 28, 1995 to Chih-Yu Hsia et al., titled "Reading Device," describes a double mirror assembly adjustably mounted on a stand, with the stand including a book rest or the like thereon. The Hsia et al. device results in relatively little change in the directional path of the reflected image, unlike the essentially ninety degree change provided by the present device, and what change is provided, is in the wrong direction for the purposes of the present invention. A person using the Hsia et al. device, could not adjust it to allow the head to remain tilted forward while still enjoying a forward view. Moreover, Hsia et al. include a concave mirror for magnifying the reflected image, which is not desirable in the present device due to the proximity of the mirrors to the eyes of the user. Also, the Hsia et al. assembly is not adaptable for placement on the lap or on a conventional tripod.

U.S. Pat. No. 5,661,860 issued on Sep. 2, 1997 to Alfred J. Heitz, titled "Eye Surgery Recovery Apparatus," describes various embodiments of a device for supporting the head and face of a person in a prone, or at least head down, position. One embodiment rests upon the edge of a bed, and includes legs for support. Another embodiment includes a four legged stand, while yet another rests upon a table top or the like. All of the embodiments of the Heitz device are adapted for a person to rest his/her head in direct contact therewith, unlike the present invention, and none of the Heitz embodiments include any mirrors or other means for the user to see anything other than the view straight through the orifice of the headrest portion of the device.

U.S. Pat. No. 5,760,865 issued on Jun. 2, 1998 to Colin Webster, titled "Glasses For Viewing Two Scenes Simultaneously," describes a device worn like a pair of eyeglasses and having semitransparent reflecting surfaces. The user may view the downward view directly through the semitransparent surfaces, but the semitransparency allows the reflected view generally above the normal line of sight of the user, to be viewed as well. The device is more closely related to the mirror assembly of the Gaxiola, Jr. U.S. Patent discussed further above, for allowing the rider of a bicycle to have a clearer forward view, than to the present invention. Webster does not provide any means of carrying or holding the device on the lap of the user, nor of mounting the device on a tripod or partially enclosing the device to reduce reflected ambient light, as provided by the present invention.

U.S. Pat. No. 5,835,294 issued on Nov. 10, 1998 to Norio Minegishi, titled "Wide-Angle Side-Mirror Device," describes a portable mirror box for observing the field of view beyond the conventional side mirrors of a truck. As such, the Minegishi device includes a mirror with a compound concave-convex curvature, for widening the horizontal field of view. As the field of view is generally to the side, in the same direction as the driver would look through the device, and somewhat to the rear, a person using the Minegishi mirror box for the purposes of the present invention would find a generally downward field of view encompassing the lower portion of their body and the floor, rather than providing a forward view. Moreover, no tripod or lap support is provided by Minegishi for his device, nor is any folding means disclosed.

U.S. Pat. No. 5,900,997 issued on May 4, 1999 to Michael Shapiro, titled "Headrest Apparatus For Forward Viewing From Face Down Position," describes a mirror box having two mirrors in the lower portion thereof, for reflecting a forward view upwardly to a downward facing viewer resting his/her head on the top of the box. The top slides to reposition the view port over a folding external shelf for holding a book or the like. The Shapiro box itself does not fold, as does the present device. Also, Shapiro does not disclose any tripod support or padding for supporting his box comfortably on the lap, as provided by the present invention. Moreover, one of the mirrors of the present invention is secured to the foldable lid of the box for a more compact arrangement, unlike the Shapiro device or others of the prior art.

U.S. Pat. No. D-391,278 issued on Feb. 24, 1998 to Su-Min Kung, titled "Periscope," illustrates a design for a periscope similar to that described in the U.S. Patent to Warnecke, described further above. While the Kung periscope apparently includes handles, the remainder of the device appears to differ from the present invention in the same respects as the Warnecke periscope, and cannot perform the function of the present device.

British Patent Publication No. 820,353 published on Sep. 16, 1959 to Barney B. Girden, titled "Improvements In Or Relating To A Face Mask Combined With A Periscopic Device For Swimmers," describes the same invention as that of the '959 U.S. Patent to the same inventor, described further above. The same differences and distinctions noted in that discussion, are seen to apply here.

British Patent Publication No. 2,045,453 published on Oct. 29, 1980 to Wong Cheung-Huang, titled "Multipurpose Optical Device," describes a magnifying device which may be used as various configurations of reflecting telescopes and microscopes. The magnifying nature of the device, and its lack of lap support means, differ from the present view box invention.

Finally, French Patent Publication No. 2,620,406 published on Mar. 17, 1989 to Lilian Christol illustrates a prism for mounting upon the handlebars of a bicycle, for the purposes described for the device of the Gaxiola Jr. U.S. Patent discussed further above. The same points raised in that discussion are seen to apply here.

None of the above inventions and patents, either singly or in combination, is seen to describe the instant invention as claimed.

SUMMARY OF THE INVENTION

The present invention comprises a vision aid for persons recovering from certain ophthalmic operations or procedures, such as surgery for retinal reattachment and macular regeneration or repair. In such procedures, a bubble of air or the like is introduced in the back of the eye to exert pressure upon the retina. In order to maintain the position of the air bubble, the patient must carry the head down with the eyes facing downwardly, nearly all of the time for at least a few weeks. This makes it all but impossible for the patient to watch television, make eye contact with others, and generally carry on normal activities during recovery.

Accordingly, the present invention provides means for the recovering patient to observe the view to the front, by means of a folding mirror box having a first mirror installed upon the interior of the base or floor of the box, and a second mirror secured to the interior surface of the folding upper surface or lid of the box. The base or floor of the box includes different means for supporting the device, including padding for supporting the device upon the lap of the user, and a tripod attachment fitting for mounting the device upon a conventional tripod, as desired. Folding the lid upwardly angles the upper or object mirror relative to the lower mirror to provide a generally horizontal field of view for a person looking downwardly into the box through a viewport in the lid, while folding the lid downwardly collapses the structure to provide for compact storage thereof when not in use.

Accordingly, it is a principal object of the invention to provide an improved vision aid for recovering ophthalmic patients, with the device providing a forward field of view for patients looking downwardly into the viewport of the device.

It is another object of the invention to provide an improved vision aid generally comprising a folding box-like structure having a floor and a hinged top or lid, with a viewing mirror secured to the upper or inner surface of the floor and an object mirror secured to the inner surface of the hinged lid.

It is a further object of the invention to provide an improved vision aid including means for securing the lid in an open position at the proper angle to position the two mirrors for turning the field of view from a generally horizontal field to a generally vertical field.

An additional object of the invention is to provide an improved vision aid including means for supporting the device upon the user's lap and/or upon a conventional tripod, as desired.

Still another object of the invention is to provide an improved vision aid including side walls for blocking entry of ambient light from other than the desired forward field of view.

It is an object of the invention to provide improved elements and arrangements thereof in an apparatus for the purposes described which is inexpensive, dependable and fully effective in accomplishing its intended purposes.

These and other objects of the present invention will become apparent upon review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
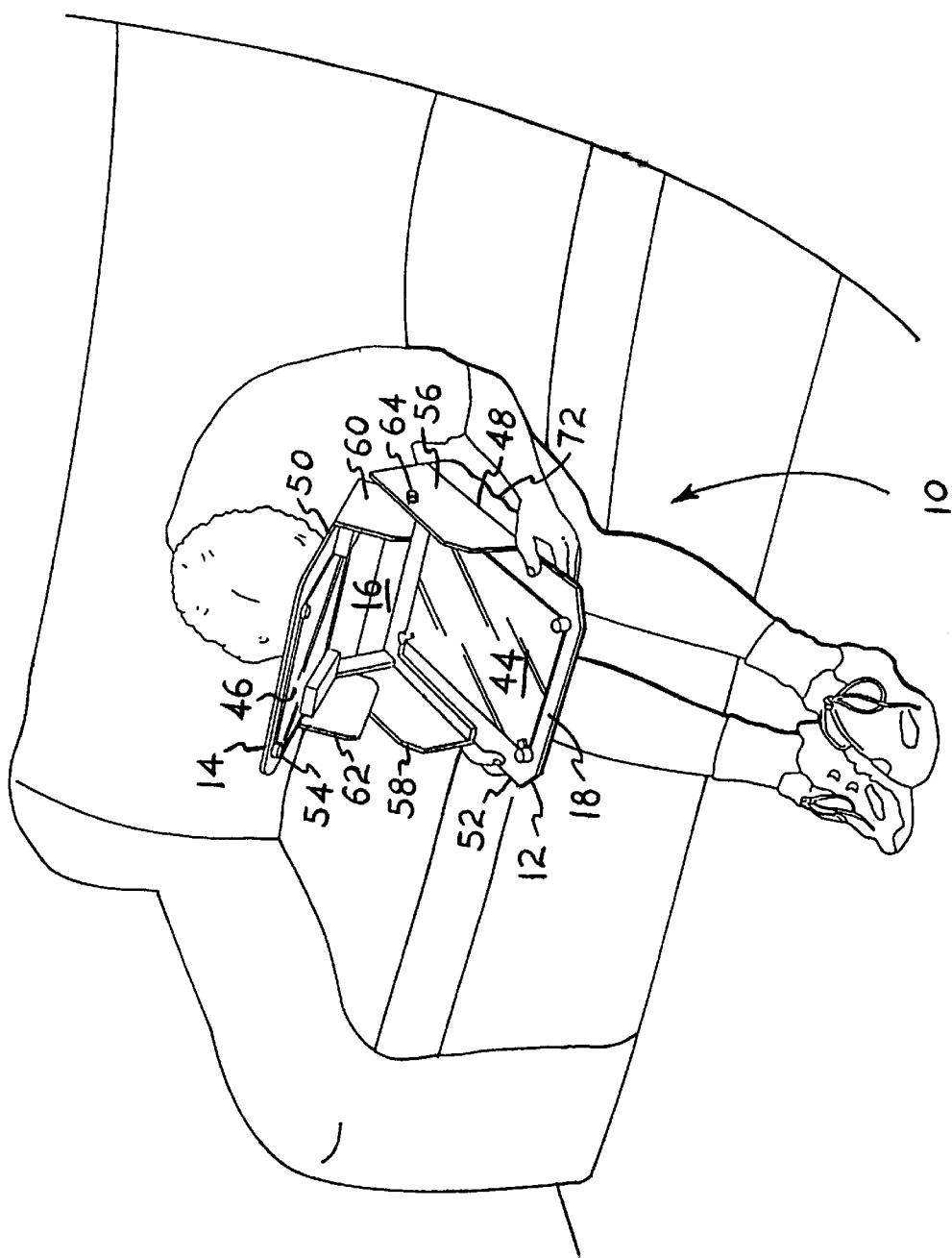
FIG. 1 is an environmental front perspective view of the present vision aid in use and resting upon the lap of the user, showing its operation.
Figure 2:
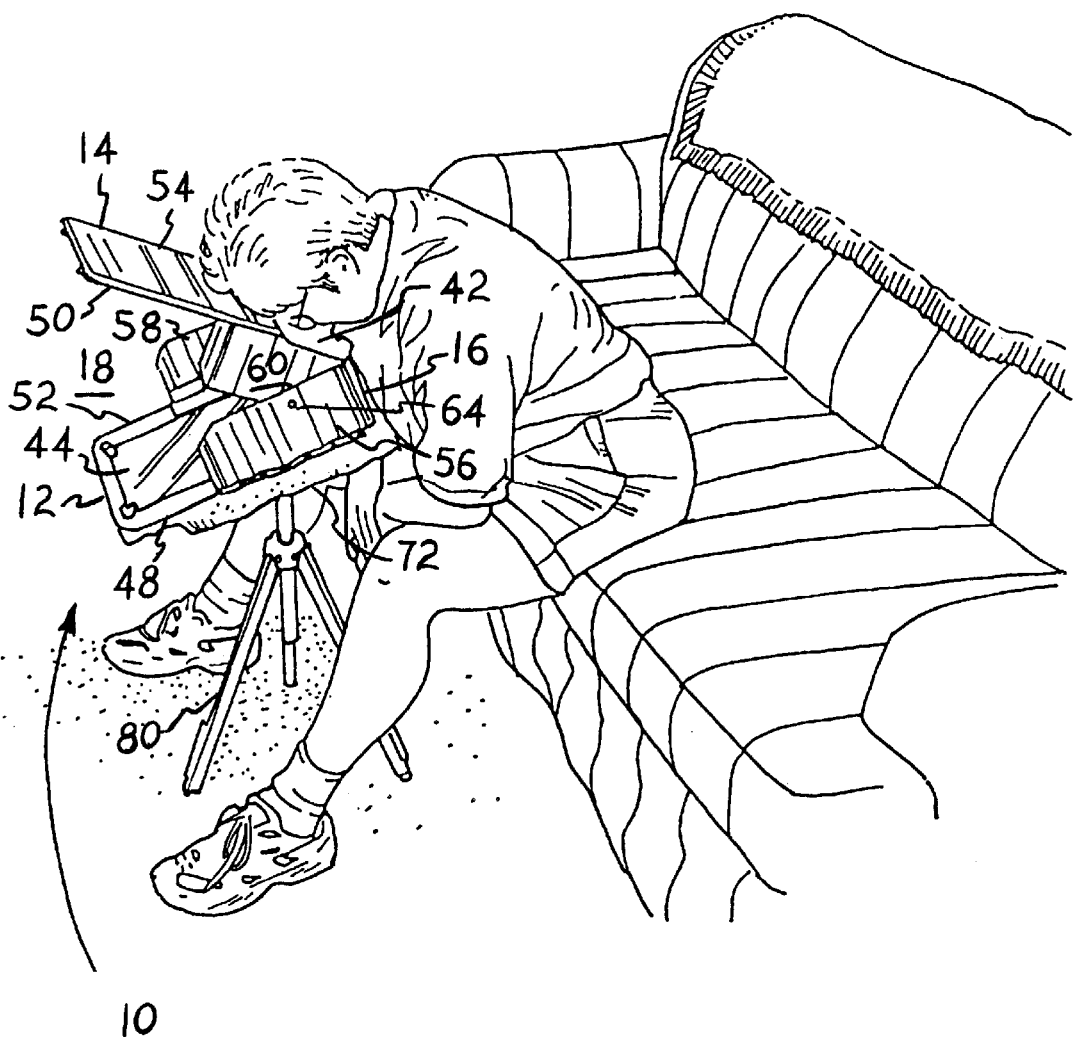
FIG. 2 is an environmental left side perspective view of the present vision aid in use, showing its installation upon a tripod.

The present invention comprises a vision aid for recovering ophthalmic patients, for providing such patients with a generally horizontal view while they hold their heads and eyes in a lowered position for proper healing of the eye. The use of the present vision aid is illustrated in FIGS. 1 and 2, with the device generally comprising a box-like structure 10 having a lower panel or floor 12, an opposite upper panel or lid 14, and a back panel or wall 16, with the front area 18 opposite the back wall 16 being open.

Figure 3:
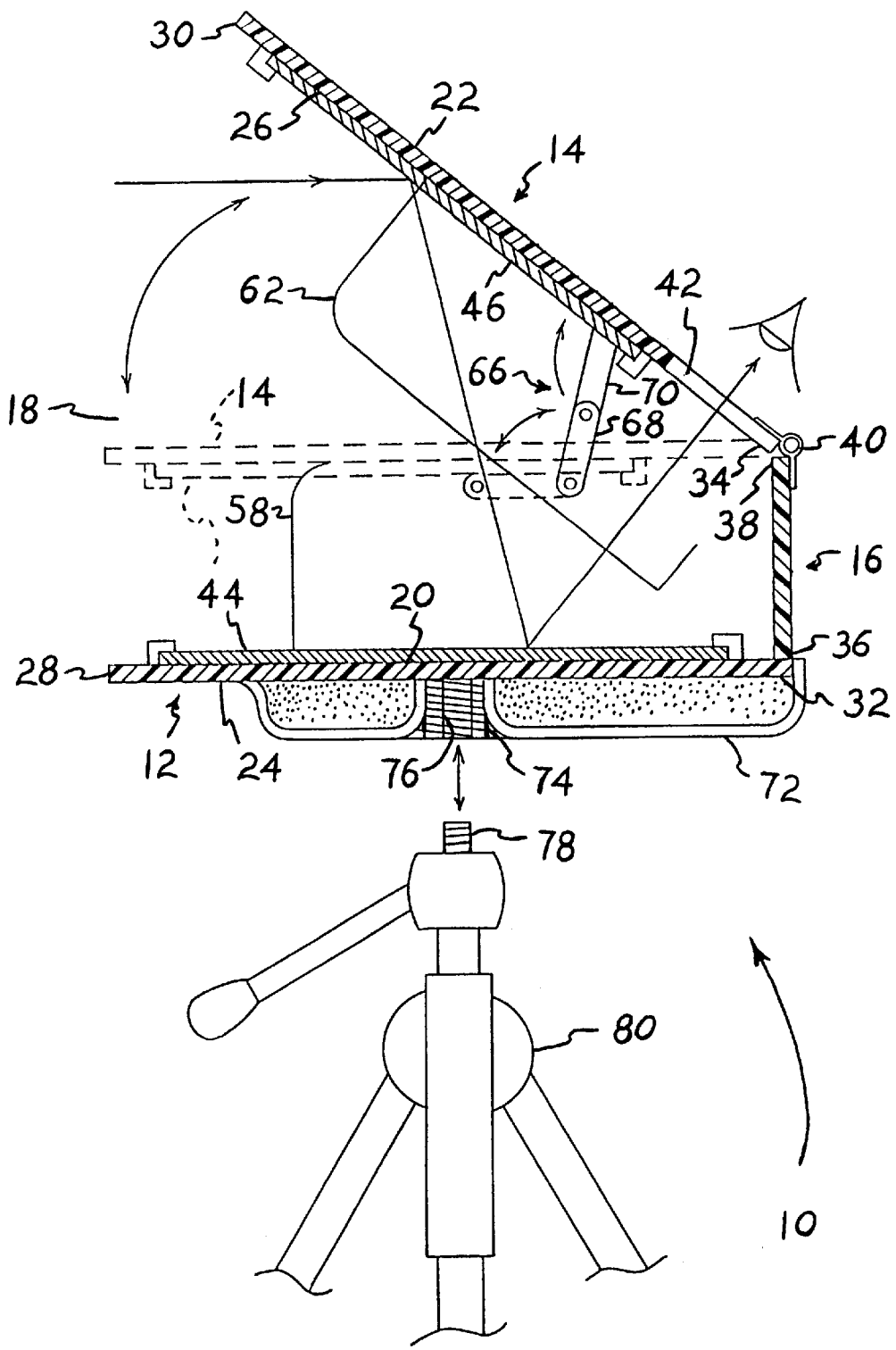
FIG. 3 is a left side elevation view in section of the present vision aid, showing various features of the structure thereof and the folding operation.

Further details are shown in the left side elevation view in section of FIG. 3. The floor 12 and lid 14 each have an upper or top surface, respectively 20 and 22, an opposite lower or bottom surface, respectively 24 and 26, a forward edge, respectively 28 and 30, and an opposite rearward edge, respectively 32 and 34. The back panel 16 has a lower edge 36 and an opposite upper edge 38, with the lower edge 36 being immovably affixed to the rearward edge 32 of the floor panel 12 so the rearward panel or wall 16 extends upwardly therefrom, with the rearward edge 34 of the lid 14 being attached to the upper edge 38 of the back wall 16 so the lid 14 extends forwardly from the back wall 16 to generally overlie the floor 12. The attachment means for securing the lid 14 to the back wall 16 preferably comprises hinges 40 positioned adjacent each lateral edge of the lid 14 and back wall 16, enabling the lid 14 to pivot arcuately upwardly, as shown by the solid line position of the lid 14 in FIG. 3, and to fold downwardly and generally parallel to the floor 12, as shown by the broken line position of the lid 14, for compact storage of the box structure 10 when it is not in use.

The rearward portion of the upper panel or lid 14 includes a viewport 42 therethrough, with the viewport 42 extending between the two widely spaced hinges 40 and somewhat toward the opposite forward end or edge 30 of the lid 14. The viewport 42 allows a user of the present vision aid to look downwardly into the interior of the box 10, to have a generally horizontal view as presented by the mirrors disposed within the interior of the box structure 10.

A viewing mirror 44 is affixed to the top surface 20 of the floor panel 12, with an object mirror 46 being affixed to the generally oppositely disposed lower or bottom surface 26 of the lid or upper panel 14. The two mirrors 44 and 46 are flat and planar, as no magnification or other modification of the image viewed through the present device is required, and generally face one another, particularly when the box structure 10 is closed for compact storage, with the floor and lid panels 12 and 14, and their corresponding mirrors 44 and 46, disposed parallel to one another. The mirrors 44 and 46 may be affixed to their respective panels 12 and 14 by means of conventional corner or edge clips or fasteners, or adhesive means, etc., as desired.

When the present vision aid 10 is to be used, the lid 14 is raised to essentially the position shown in FIGS. 1 and 2 and indicated in solid lines in FIG. 3. The upper object mirror 46 is disposed at or near a forty five degree angle to the floor 12 and its viewing mirror 44, with the rearward edges 32 and 34 of the floor 12 and lid 14 closer to one another than their respective forward edges 28 and 30, with their corresponding mirrors 44 and 46 also positioned with the same relationship when the box structure 10 is opened for use. With the floor 12 and its viewing mirror 44 positioned generally horizontally, light from the scene in front of the device 10 enters the open forward end 18 of the box structure 10 and reflects from the raised object mirror 46, generally downwardly to reflect from the viewing mirror 44, and upwardly and rearwardly to pass through the viewport 42, as shown in FIG. 3.

The present invention includes means for holding or locking the lid or upper panel 14 of the box 10 in the desired position for use, and for reducing glare from any laterally disposed lighting. The floor 12 and lid 14 each have first lateral edges, respectively 48 and 50, and opposite second lateral edges, respectively 52 and 54, as indicated in FIGS. 1 and 2. Each of these edges 48 through 54 has a panel extending therefrom, with the first and second lateral edges 48 and 52 of the floor panel 12 respectively having first and second floor sidewalls 56 and 58 extending upwardly therefrom, and the first and second lateral edges 50 and 54 of the lid respectively having first and second lid sidewalls 60 and 62 extending downwardly therefrom. The first sidewalls 56, 60 and second sidewalls 58, 62 essentially completely overlap one another when the box structure 10 is folded closed, and at least partially overlap one another when the structure is opened for use. These sidewall panels 56 through 62 serve to limit lateral light entry into the device 10, and also provide for locking means for holding the lid 14 in an open position for use of the device 10.

Various different types of locking means may be provided for securing the lid 14 of the present vision aid 10 in an open position for use. In FIGS. 1 and 2, the two first (left side) sidewalls 56 and 60 are provided with conventional holes therethrough, comprising lock pin passages which are aligned with one another when the lid 14 is opened to the proper angle. A removable locking pin 64 is inserted through the two passages to lock the lid 14, and its object mirror 46, at the desired angle.

FIG. 3 discloses an alternative locking means for holding the lid 14 open as desired. In FIG. 3, an articulated folding arm 66 comprises a first link 68 secured to the floor sidewall 58, with a second link 70 connected to the lid sidewall 62. The two links 68 and 70 are attached to facing walls of the two panels 58 and 62, to fold therebetween when the box structure 10 is folded closed. Opening the structure 10 generally to the position shown in solid lines in FIG. 3, extends the two links 68 and 70 to straighten the arm 66 and hold the lid 14 open relative to the floor 12 for use. The box 10 is closed by folding the two links 68 and 70 and closing the lid 14 downwardly to lie essentially parallel to the floor 12. While the arm 66 is shown connecting the two right sidewalls 58 and 62 together, it will be seen that such a link could be used on the left side of the structure 10 in lieu of, or in addition to, the right side link shown in FIG. 3. In a similar manner, the lock pin passage and lock pin 64 shown with the left sidewall panels 56 and 60 in FIGS. 1 and 2, could be added to the opposite right sidewall panels 58 and 62, if desired.

The present vision aid 10 may be used in various ways, as by placement upon the lap of a person using the device as shown in FIG. 1, or by installing the device upon a conventional camera tripod or the like, as shown in FIG. 2 of the drawings. The lower or bottom surface 24 of the floor panel 12 is provided with a soft, resilient upholstery or padding material 72 (e. g., foam, natural or synthetic fiber, etc.) and soft, pliable covering for user comfort when the device is placed upon the lap.

The cross section elevation view of FIG. 3 also discloses the tripod attachment fitting 74 disposed in the general center of the bottom surface 24 of the floor panel 12. The tripod fitting 74 comprises a conventional fitting having an internally threaded receptacle 76 therein, for mating attachment to the conventional externally threaded stud 78 of a conventional camera tripod 80 or the like. In this manner, the present vision aid 10 may be installed upon a tripod 80, as shown in FIG. 2 of the drawings, to remain clear of the lap of the user and permit hands free use of the present invention.

Figure 4:
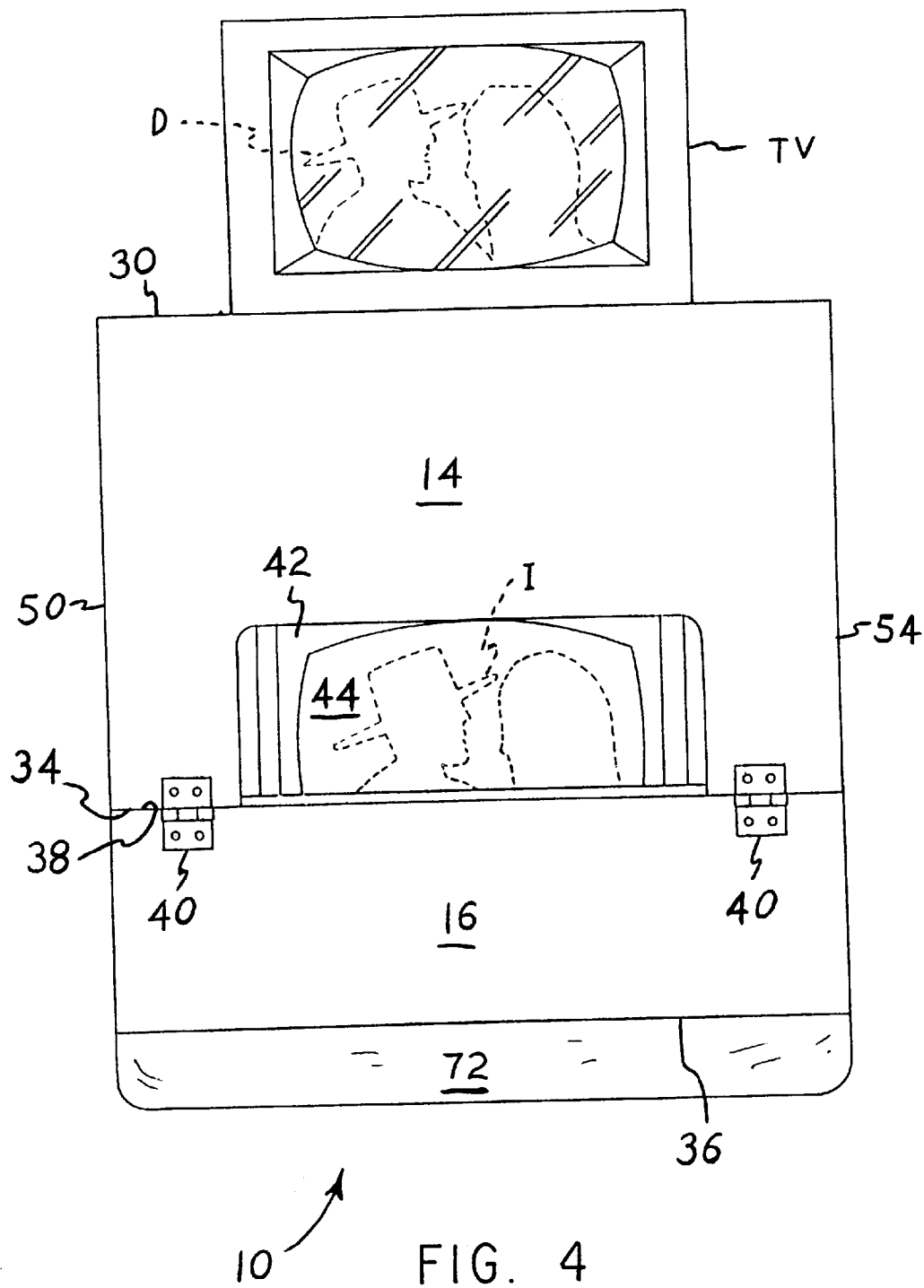
FIG. 4 is a top and rear perspective view of the present vision aid, showing a portion of the view through the viewport.

FIG. 4 illustrates a view of the present device 10 generally from the top and rear of the structure. The upper lid 14 has been opened to properly deploy the object and viewing mirrors for use. The device 10 is oriented toward a television set TV, for a user of the device to view the program being played. The display D of the television picture enters the front of the box structure 10, as shown in FIG. 3, and is reflected from the object mirror 46 (FIG. 3) generally downwardly to the viewing mirror 44. The image I viewed through the viewport 42 is correct, as shown in FIG. 4, and is not reversed due to its double reflection from the two mirrors 46 and 44. Lowering the eyes and face toward the opened lid 14 to look downwardly through the viewport 44, provides the user with an excellent, undistorted image I of the display D being shown on the television set TV, or any other view toward which the device 10 is oriented, e. g., toward another person for conversation, a scenic view, etc., as desired.

In summary, the present vision aid for recovering ophthalmic patients enables such persons to hold their heads, and particularly their eyes, in a lowered position to promote proper post surgical healing, while still being able to enjoy a generally horizontal field of view. The floor, lid, back wall, and side walls of the present device may be formed of virtually any practicable sheet material, such as wood, plastic, metal, etc. The use of wood or plastic, in combination with mirrors of reflectively coated clear acrylic material or the like, provides an extremely lightweight structure which is easily and comfortably supported upon the lap of a user of the device. The provision for tripod attachment provides further versatility for the present device.

Extension of the lid to the proper angle for presenting a complete image through the viewport is easily accomplished by aligning the two lock pin passages and inserting the lock pin, or extending the arm links, depending upon the embodiment of the invention. The folding of the lid of the structure provides an extremely compact configuration for storage of the device when not in use. Accordingly, the present vision aid device will prove to be a most valuable and highly appreciated tool for persons recovering from eye surgery where the head and eyes must be retained in a lowered position, enabling them to conduct many activities which would otherwise be difficult or impossible.

It is to be understood that the present invention is not limited to the embodiments described above, but encompasses any and all embodiments within the scope of the following claims.

I claim:

1. A vision aid for recovering ophthalmic patients, comprising:

a generally box-like structure including at least a floor, a lid, an open front, and a back wall;

said floor and said lid each having a top surface, a bottom surface, a forward edge, and a rearward edge;

a flat, planar viewing mirror affixed to said top surface of said floor;

a flat, planar object mirror affixed to said bottom surface of said lid, and generally facing said viewing mirror;

said back wall having a lower edge immovably affixed to said rear edge of said floor and extending upwardly therefrom, and an upper edge;

said rearward edge of said lid being arcuately secured to said upper edge of said back wall by hinge means for folding said lid parallel to said floor for storage;

a viewport formed through said lid, adjacent said rearward edge thereof, for viewing said viewing mirror therethrough; and said floor and said lid, with said viewing mirror and said object mirror respectively affixed thereto, being positioned in a non-parallel relationship with each said rearward edge being closer to one another than each said forward edge when said box-like structure is in use, with light passing generally horizontally through said open front, reflecting from said object mirror to said viewing mirror, and passing generally upwardly through said viewport.

2. The vision aid according to claim 1, including locking means for holding said lid open relative to said floor.

3. The vision aid according to claim 1, wherein:

said floor and said lid each include a first lateral edge and a second lateral edge opposite thereto;

said first and said second lateral edge of said floor respectively having a first and an opposite second floor sidewall extending upwardly therefrom;

said first and said second lateral edge of said lid respectively having a first and an opposite second lid sidewall extending downwardly therefrom; and each corresponding said floor sidewall and said lid sidewall at least partially overlapping one another for limiting lateral light entrance to said structure.

4. The vision aid according to claim 3, wherein at least said floor, said lid, said back wall, each said floor sidewall, and each said lid sidewall are each formed of materials selected from the group consisting of wood, plastic, and metal.

5. The vision aid according to claim 3, wherein:

said rearward edge of said lid and said upper edge of said back wall are arcuately secured together by hinge means for folding said lid parallel to said floor for storing said structure when not in use;

said structure including locking means for holding said lid open relative to said floor;

said locking means comprising lock pin passages formed through at least one said floor sidewall and corresponding said lid sidewall;

said lock pin passages being aligned with one another when said structure is opened for use; and a locking pin removably installable through said lock pin passages for locking said at least one floor sidewall and said corresponding said lid sidewall relative to one another, for holding said lid open relative to said floor.

6. The vision aid according to claim 3, wherein:

said rearward edge of said lid and said upper edge of said back wall are arcuately secured together by hinge means for folding said lid parallel to said floor for storing said structure when not in use;

said structure including locking means for holding said lid open relative to said floor;

said locking means comprising at least one articulated folding arm having a first link secured to at least one said floor sidewall and a second link secured to a corresponding said lid sidewall, for locking said at least one floor sidewall and said corresponding said lid sidewall relative to one another, for holding said lid open relative to said floor when said folding arm is extended.

7. The vision aid according to claim 1, including resilient padding disposed upon said bottom surface of said floor, for supporting said structure comfortably upon the lap of a user.

8. A vision aid for recovering ophthalmic patients, comprising:

a generally box-like structure including at least a floor, a lid, an open front, and a back wall;

said floor and said lid each having a top surface, a bottom surface, a forward edge, and a rearward edge;

a tripod attachment depending from said bottom surface of said floor, for removably securing and supporting said structure upon a tripod;

a flat, planar viewing mirror affixed to said top surface of said floor;

a flat, planar object mirror affixed to said bottom surface of said lid, and generally facing said viewing mirror;

said back wall having a lower edge immovably affixed to said rear edge of said floor and extending upwardly therefrom, and an upper edge;

said rearward edge of said lid being secured to said upper edge of said back wall, with said lid extending forwardly from said back wall and overlying said floor;

a viewport formed through said lid, adjacent said rearward edge thereof, for viewing said viewing mirror therethrough; and said floor and said lid, with said viewing mirror and said object mirror respectively affixed thereto, being positioned in a non-parallel relationship with each said rearward edge being closer to one another than each said forward edge when said box-like structure is in use, with light passing generally horizontally through said open front reflecting from said object mirror to said viewing mirror, and passing generally upwardly through said viewport.

9. The vision aid according to claim 8, including a tripod.

10. A vision aid for recovering ophthalmic patients, comprising:

a generally box-like structure including at least a floor, a lid, an open front, and a back wall;

said floor and said lid each having a top surface, a bottom surface, a forward edge, and a rearward edge;

a flat, planar viewing mirror affixed to said top surface of said floor;

a flat, planar object mirror affixed to said bottom surface of said lid, and generally facing said viewing mirror;

said back wall having a lower edge immovably affixed to said rear edge of said floor and extending upwardly therefrom, and an upper edge;

hinge means arcuately securing said rearward edge of said lid to said upper edge of said back wall for folding said lid parallel to said floor for storage, with said lid extending forwardly from said back wall and overlying said floor;

a viewport formed through said lid, adjacent said rearward edge thereof, for viewing said viewing mirror therethrough; and said floor and said lid, with said viewing mirror and said object mirror respectively affixed thereto, being positioned in a non-parallel relationship with each said rearward edge being closer to one another than each said forward edge when said box-like structure is in use, with light passing generally horizontally through said open front, reflecting from said object mirror to said viewing mirror, and passing generally upwardly through said viewport.

11. The vision aid according to claim 10, including locking means for holding said lid open relative to said floor.

12. The vision aid according to claim 10, wherein:

said floor and said lid each include a first lateral edge and a second lateral edge opposite thereto;

said first and said second lateral edge of said floor respectively having a first and an opposite second floor sidewall extending upwardly therefrom;

said first and said second lateral edge of said lid respectively having a first and an opposite second lid sidewall extending downwardly therefrom; and each corresponding said floor sidewall and said lid sidewall at least partially overlapping one another for limiting lateral light entrance to said structure.

13. The vision aid according to claim 12, wherein at least said floor, said lid, said back wall, each said floor sidewall, and each said lid sidewall are each formed of materials selected from the group consisting of wood, plastic, and metal.

14. The vision aid according to claim 12, wherein:

said structure including locking means for holding said lid open relative to said floor;

said locking means comprising lock pin passages formed through at least one said floor sidewall and corresponding said lid sidewall;

said lock pin passages being aligned with one another when said structure is opened for use; and a locking pin removably installable through said lock pin passages for locking said at least one floor sidewall and said corresponding said lid sidewall relative to one another, for holding said lid open relative to said floor.

15. The vision aid according to claim 12, wherein:

said structure including locking means for holding said lid open relative to said floor;

said locking means comprising at least one articulated folding arm having a first link secured to at least one said floor sidewall and a second link secured to a corresponding said lid sidewall, for locking said at least one floor sidewall and said corresponding said lid sidewall relative to one another, for holding said lid open relative to said floor when said folding arm is extended.

16. The vision aid according to claim 10, including resilient padding disposed upon said bottom surface of said floor, for supporting said structure comfortably upon the lap of a user.

17. The vision aid according to claim 10, including a tripod attachment depending from said bottom surface of said floor, for removably securing and supporting said structure upon a tripod.

18. The vision aid according to claim 17, including a tripod.

* * * * *